United States Patent
Bugni et al.

(10) Patent No.: US 11,135,203 B2
(45) Date of Patent: *Oct. 5, 2021

(54) FORAZOLINES, COMPOSITIONS THEREOF AND USES THEREOF

(71) Applicant: Wisconsin Alumni Research Foundation, Madison, WI (US)

(72) Inventors: Timothy Bugni, Madison, WI (US); Thomas Wyche, Chelsea, MA (US); David Andes, Madison, WI (US); Douglas Braun, Mount Horeb, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,456

(22) Filed: May 1, 2018

(65) Prior Publication Data

US 2018/0243269 A1    Aug. 30, 2018

Related U.S. Application Data

(63) Continuation of application No. 15/146,672, filed on May 4, 2016, now abandoned, which is a continuation of application No. 14/299,953, filed on Jun. 9, 2014, now Pat. No. 9,346,828.

(60) Provisional application No. 61/832,597, filed on Jun. 7, 2013.

(51) Int. Cl.
| | |
|---|---|
| *C07D 513/18* | (2006.01) |
| *A61K 31/7048* | (2006.01) |
| *C07H 17/08* | (2006.01) |
| *A61K 31/429* | (2006.01) |
| *A61K 31/7052* | (2006.01) |
| *A61K 45/06* | (2006.01) |

(52) U.S. Cl.
CPC ........ *A61K 31/429* (2013.01); *A61K 31/7048* (2013.01); *A61K 31/7052* (2013.01); *A61K 45/06* (2013.01); *C07D 513/18* (2013.01); *C07H 17/08* (2013.01)

(58) Field of Classification Search
None
See application file for complete search history.

(56) References Cited

U.S. PATENT DOCUMENTS

2011/0118323 A1    5/2011 Luesch et al.

FOREIGN PATENT DOCUMENTS

WO    WO-2012/076989 A1    6/2012

OTHER PUBLICATIONS

Andes, D. et al., "Pharmacodynamics of Amphotericin B in a Neutropenic-Mouse Disseminated-Candidiasis Model," Antimicrobial Agents and Chemotherapy, (Mar. 2001), vol. 45, No. 3, pp. 922-926.
TransWorld News, "Antifungal Drugs: Technologies and Global Markets—new market research report," London, (published May 27, 2011), printed Nov. 14, 2014 from http://www.transworldnews.com/743457/c1/Default.aspx, 2 pages.
U.S. Notice of Allowance on U.S. Appl. No. 14/299,953 dated Jan. 29, 2016 (7 pages).
U.S. Office Action for U.S. Appl. No. 14/299,953 dated Sep. 5, 2015 (12 pages).
U.S. Office Action on U.S. Appl. No. 15/146672 dated Nov. 1, 2017.
Wilson, Leslie S. et al., "The Direct Cost and Incidence of Systemic Fungal Infections," Value in Health, (Jan. 2002), vol. 5, Issue 1, pp. 26-34.
Wyche, Thomas P. et al., "First Natural Analogs of the Cytotoxic Thiodepsipeptide Thiocoraline A from a Marine *Verrucosispora* sp.," J. Org. Chem., (Aug. 19, 2011), vol. 76, No. 16, pp. 6542-6547.

*Primary Examiner* — Leigh C Maier

(74) *Attorney, Agent, or Firm* — Foley & Lardner LLP

(57) ABSTRACT

An isolated compound of Formula I and salts thereof are provided:

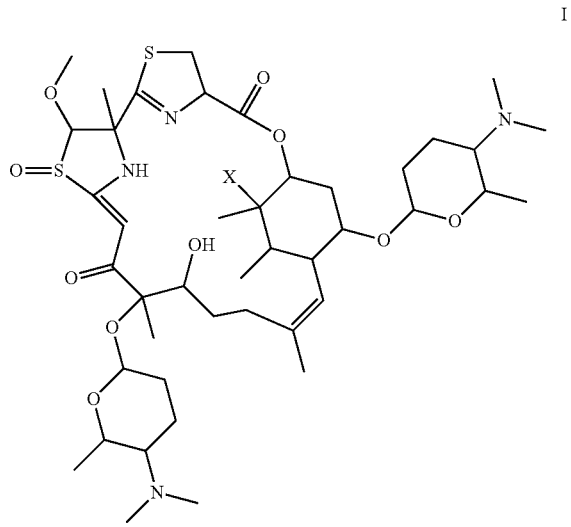

wherein X is Cl or Br. A compound isolated from *Actinomadura* and having a chemical formula of $C_{43}H_{69}ClN_4O_{10}S_2$ or $C_{43}H_{69}BrN_4O_{10}S_2$ is also provided. Compositions including the compounds and methods of using the compounds to treat fungal infections including those such as *Candida* are also disclosed.

21 Claims, 12 Drawing Sheets

FORAZOLINES, COMPOSITIONS THEREOF AND USES THEREOF

CROSS-REFERENCE TO RELATED APPLICATIONS

This application is a continuation of U.S. patent application Ser. No. 15/146,672, filed on May 4, 2016, which is a continuation of U.S. application Ser. No. 14/299,953, filed on Jun. 9, 2014, now U.S. Pat. No. 9,346,828, issued on May 24, 2016, which claims priority to U.S. Provisional Application No. 61/832,597, filed on Jun. 7, 2013, the contents of which are incorporated by reference in their entirety into the present disclosure.

STATEMENT OF GOVERNMENT SUPPORT

This invention was made with government support under GM092009 awarded by the National Institutes of Health. The government has certain rights in the invention.

FIELD OF THE TECHNOLOGY

The present technology relates to a new class of compounds called Forazolines, compositions and methods of use thereof. Specifically, new isolated compounds useful as antifungals are disclosed herein.

SUMMARY

A new compound, called Forazoline A, as well as other Forazolines has been discovered and isolated from *Actinomadura*, a bacterium collected from a species of sea squirt. Forazoline A has the chemical formula $C_{43}H_{69}ClN_4O_{10}S_2$ and is water soluble (e.g., about 5 mg/mL). The isolated compound exhibits $^{15}N$ NMR peaks at about 140.2 ppm and about 302.6 ppm and an $^1H$ NMR peak at about 14.58 ppm. The isolated compound further exhibits $^{13}C$ NMR peaks at about 76.2 ppm, about 78.2 ppm, about 166.5 ppm, about 170.3 ppm, and about 212.0 ppm. The isolated compound exhibits an IR band at about 1060 cm$^{-1}$. Pharmaceutical compositions including forazaoline (or pharmaceutically acceptable salts thereof) and a pharmaceutically acceptable carrier are provided. Methods of treating fungal infections (such as *Candida*) by administering Forazoline to a mammal in need thereof are disclosed.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
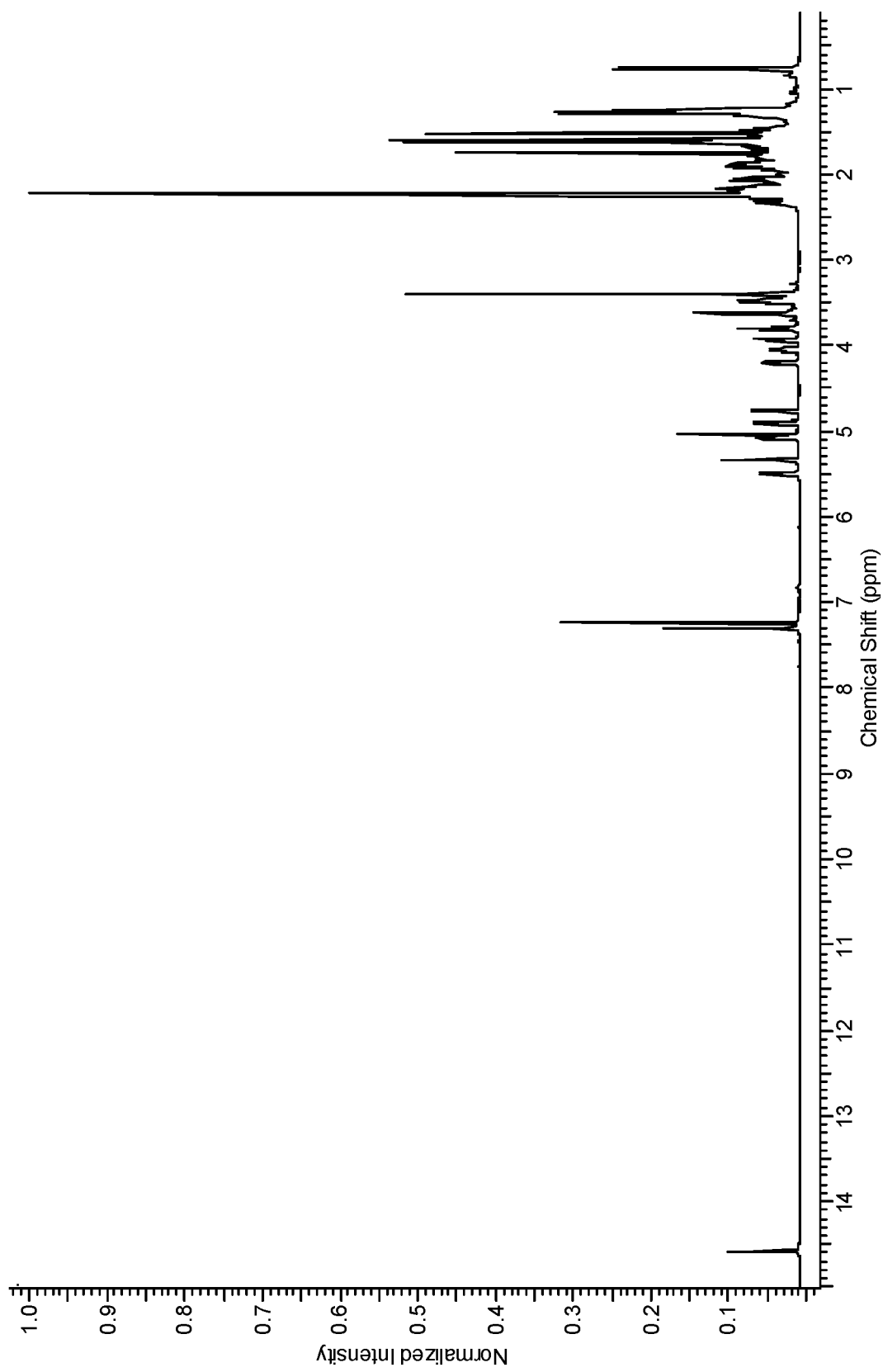
FIG. 1 shows an $^1H$ NMR (600 MHz, CDCl$_3$) spectrum of Forazoline A.

The present technology provides an isolated compound useful for the treatment of fungal infections such as those caused by the yeast *Candida*. Thus, in accordance with one aspect, the technology includes a compound isolated from *Actinomadura* sp. (strain WMMB-499) and having a chemical formula of $C_{43}H_{69}ClN_4O_{10}S_2$ or $C_{43}H_{69}BrN_4O_{10}S_2$ and salts thereof, including but not limited to, pharmaceutical salts thereof.

The present technology further provides an isolated compound having a chemical formula of $C_{43}H_{69}ClN_4O_{10}S_2$ (and salts thereof) may exhibit $^{15}N$ NMR peaks at about 140.2 ppm and about 302.6 ppm and an $^1H$ NMR peak at about 14.58 ppm. In some embodiments, the isolated compound may exhibit $^{13}C$ NMR peaks at about 76.2, about 78.2, about 166.5, about 170.3 ppm, and about 212.0 ppm. In other embodiments, the isolated compound having a chemical formula of $C_{43}H_{69}ClN_4O_{10}S_2$ (and salts thereof) may exhibit an IR band at about 1060 cm$^{-1}$. The term "about" will be understood by those of skill in the art to include values within ±2% of the stated value.

In another embodiment, the present technology provides an isolated compound of Formula I:

I and salts thereof, wherein X is Cl or Br.

In some embodiments, the isolated compound (and salts thereof) has Formula IA, 1B or 1C:

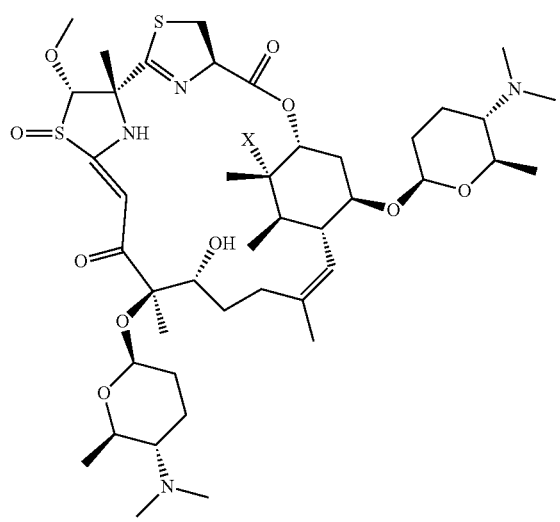

wherein X is Cl or Br.

The compounds described herein may be isolated at various purities, e.g., a purity of at least 60 wt %, at least 70 wt %, at least 80 wt %, at least 90 wt %, at least 95 wt %, at least 96, at least 97 wt %, at least 98 wt %, at least 99 wt % or at least 99.5 wt %.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereoisomeric or geometric isomeric forms, it should be understood that the technology encompasses any tautomeric, conformational isomeric, stereoisomeric and/or geometric isomeric forms of the compounds having one or more of the utilities described herein, as well as mixtures of these various different forms.

Stereoisomers of compounds (also known as optical isomers) include all chiral, diastereomeric, and racemic forms of a structure, unless the specific stereochemistry is expressly indicated. Thus, compounds disclosed herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Salts, including pharmaceutically acceptable salts of the disclosed compounds are within the scope of the present technology. When the compound has a basic group, such as, for example, an amine group, pharmaceutically acceptable salts can be formed with inorganic acids (such as hydrochloric acid, sulfuric acid, and phosphoric acid), organic acids (e.g. formic acid, acetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid).

In another aspect the present technology provides a pharmaceutical composition including any of the isolated compounds described herein or a pharmaceutical salt thereof, and a pharmaceutically acceptable carrier. Pharmaceutical compositions of the present technology may be formulated for oral, parenteral, nasal, or topical administration.

In some embodiments, there is provided a pharmaceutical composition including a compound of Formula I, or pharmaceutically acceptable salt thereof, and a pharmaceutically acceptable carrier, wherein Formula I has the structure:

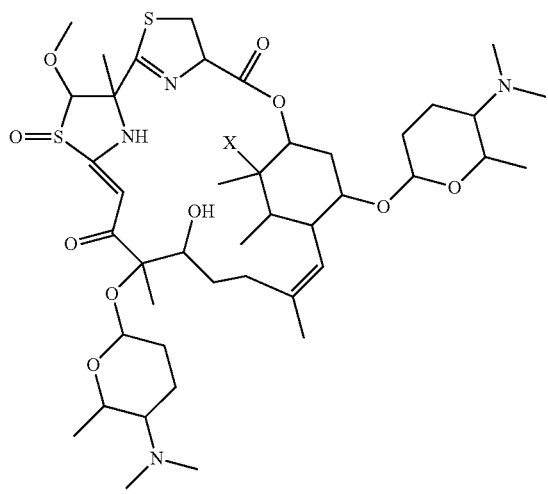

I wherein X is Cl or Br.

In some embodiments, the pharmaceutical composition includes a compound of Formula IA, IB, IC, or a pharmaceutically acceptable salt thereof, and a pharmaceutically acceptable carrier, wherein Formula IA has the structure:

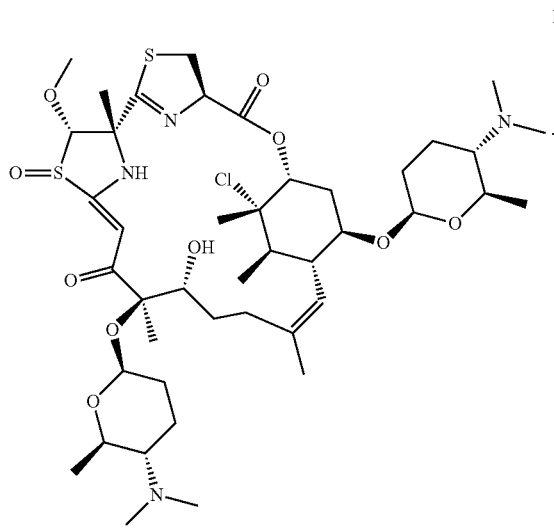

IA

In some embodiments, the pharmaceutical compositions described herein are formulated for oral, parenteral, nasal, or topical administration.

In another aspect, the present technology provides a method of treating a fungal infection comprising administering an effective amount of a compound, a salt thereof, or a pharmaceutical composition as described herein to a mammal in need thereof. The mammal may be, e.g., a human, primate (e.g. monkey, chimpanzee, ape), cat, dog, pig, mouse, rat, horse, sheep, among others. In some embodiments, the mammal is human. The infection may occur, e.g., in the skin, mouth, pharynx, esophagus, toenails, fingernails, and genitalia (including vagina and penis), or may be systemic, in, e.g., immunocompromised patients. In certain embodiments of the present methods, the fungal infection is caused by *Candida*, e.g., *Candida albicans, Candida enolase, Candida tropicalis, Candida glabrata, Candida krusei, Candida parapsilosis, Candida stellatoidea, Candida parakawsei, Candida lusitaniae, Candida pseudotropicalis*, and *Candida guilliermondi*.

In yet another aspect the present technology provides a compound as described herein, for use in therapy, such as for treatment of fungal infections. In some embodiments, the fungal infection is caused by *Candida*, e.g., *Candida albicans*. In still other embodiments, the present technology provides any of the compounds described herein for use in the manufacture of a medicament for treating a fungal infection. The fungal infection may be caused by *Candida*, e.g., *Candida albicans*.

In another aspect, the present technology provides pharmaceutical compositions of the herein-described compounds (including but not limited to compounds of Formula I, IA, IB, IC, and II) with a second antifungal agent, e.g., amphotericin B, as well as methods of using the same. Antifungal agents include drugs which demonstrate clinical benefit in treatment of fungal infections in a mammal, including a human. In some embodiments, an effective amount of a compound as described herein (including but not limited to compounds of Formulae I, IA, IB, IC, and II), a salt thereof, or a pharmaceutical composition comprising the compound or salt thereof, and a pharmaceutically acceptable carrier is administered a mammal in need thereof, wherein amphotericin B is administered to the mammal in need thereof simultaneously, sequentially or separately with a compound as described herein, the salt thereof or the pharmaceutical composition. While not wishing to be bound by theory, it is believed that the compounds described herein produce their antifungal activity by affecting the membrane permeability of the fungal cells. In some embodiments the combination of a compound described herein and a second antifungal agent is synergistic and synergistically effective amounts of the compound and/or second agent may be used. That is, lower amounts of the compound and/or agent may be used than would be the case if the therapeutic effects of the compounds and/or agents were merely additive. In some embodiments the second agent may be selected from amphotericin B, ketoconazole, terbinafine, nystatin, fluconazole, itraconazole, and voriconazole. In other embodiments the second agent is selected from imidazole-type agents, triazoles-type agents, terbinafine, and nystatin. Imidazole-type antifungal agents contain imidazole as part of their chemical structure, while triazoles-type antifungal agents contain a triazoles as part of their chemical structure.

"Treating" within the context of the instant technology, means an alleviation, in whole or in part, of symptoms associated with a disorder or disease, or slowing, inhibition or halting of further progression or worsening of those symptoms, or prevention or prophylaxis of the disease or disorder in a subject at risk for developing the disease or disorder. For example, within the context of treating fungal infections such as those caused by *Candida*, successful treatment may include clinical benefit, an alleviation of symptoms, such as a reduction or elimination of redness, itching, discomfort and/or thrush.

As used herein, an "effective amount" of a compound of the present technology refers to an amount of the compound that alleviates, in whole or in part, symptoms associated with a disorder or disease, or slows or halts of further progression or worsening of those symptoms, or prevents or provides prophylaxis for the disease or disorder in a subject at risk for developing the disease or disorder.

The instant technology also provides for compositions and medicaments including a compound disclosed herein and a pharmaceutically acceptable carrier. Such compositions may be prepared by mixing one or more compounds of the present technology, pharmaceutically acceptable salts thereof or stereoisomers thereof, with pharmaceutically acceptable carriers, excipients, binders, diluents or the like to treat fungal infections caused by *Candida*. The compounds and compositions of the present technology may be used to prepare formulations and medicaments that treat a variety of *Candida* infections, e.g., *Candida albicans*. Such compositions can be in the form of, for example, granules, powders, tablets, capsules, creams, ointments, syrup, suppositories, injections, emulsions, elixirs, suspensions or solutions. The instant compositions can be formulated for various routes of administration, for example, by oral, parenteral, topical, injection, rectal, nasal, vaginal, or via implanted reservoir. Parenteral or systemic administration includes, but is not limited to, subcutaneous, intravenous, intraperitoneally, intramuscular, intrathecal, intracranial, and intracerebroventricular injections. The following dosage forms are given by way of example and should not be construed as limiting the instant technology.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions, which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology also may be formulated as a composition for topical administration (e.g., vaginal cream). These formulations may contain various excipients known to those skilled in the art. Suitable excipients may include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

In some embodiments, the composition is in the form of a vaginal cream containing the composition of matter as set forth herein present in a nonliquefying base. The nonliquefying base may contain various inactive ingredients such as, for example, cetyl esters wax, cetyl alcohol, white wax, glyceryl monostearate, propylene glycol monostearate, methyl stearate, benzyl alcohol, sodium lauryl sulfate, glycerin, and mineral oil. Such composition may be formulated similar to PREMARIN® Vaginal Cream made commercially available by Wyeth-Ayerst Laboratories.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the present technology.

Aerosols containing compounds for use according to the present technology are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present technology using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant technology.

A therapeutically effective amount of a compound of the present technology may vary depending upon the route of administration and dosage form. Effective amounts of such compounds typically fall in the range of about 0.01 up to about 100 mg/kg/day, or about 0.05 to about 50 mg/kg/day, and more typically in the range of about 0.1 up to 5 mg/kg/day. Typically, the compound or compounds of the instant technology are selected to provide a formulation that exhibits a high therapeutic index. The therapeutic index is the dose ratio between toxic and therapeutic effects and can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology is further illustrated by the following examples, which should not be construed as limiting in any way.

EXAMPLES

General Experimental Procedures

Optical rotations were measured on a Perkin-Elmer 241 Polarimeter. Ultraviolet (UV) spectra were recorded on an Aminco/OLIS UV-Vis spectrophotometer. Infrared (IR) spectra were measured with a Bruker Equinox 55/S FT-IR spectrophotometer. Nuclear magnetic resonance (NMR) spectra were obtained in $CDCl_3$ with a Bruker Avance 600 MHz spectrometer equipped with a 1.7 mm $^1H\{^{13}C/^{15}N\}$ cryoprobe and a Bruker Avance 500 MHz spectrometer equipped with a $^{13}C/^{15}N\{^1H\}$ cryoprobe. High resolution mass spectrometry (HRMS) data were acquired with a Bruker MaXis 4G QTOF mass spectrometer. Reverse phase high pressure liquid chromatography (RP HPLC) was performed using a Shimadzu Prominence HPLC system with a Phenomenex Luna $C_{18}$ column (250×10 mm, 5 μm) and a Gilson HPLC system with a Phenomenex Gemini $C_{18}$ column (100×30 mm, 5 μm).

Example 1

Isolation of Forazoline a from Bacteria Associated with *Ascidiacea*

Biological Material. Ascidian specimens were collected in the Florida Keys (24° 39.591', 81° 25.217'). A voucher specimen (FLK10-5-6) for *Ecteinascidia turbinata* (Herdman, 1880) is housed at the University of Wisconsin-Madison. For cultivation, a sample of ascidian (1 cm³) was rinsed with sterile seawater, macerated using a sterile pestle in a micro-centrifuge tube, and dilutions were made in sterile seawater, with vortexing between steps to separate bacteria from heavier tissues. Dilutions were separately plated on three media: ISP2, R2A, and M4. Each medium was supplemented with 50 μg/mL cycloheximide and 25 μg/mL nalidixic acid. Plates were incubated at 28° C. for at least 28 days. *Actinomadura* sp. strain WMMB-499 was isolated from ISP2 medium.

Sequencing. 16S rDNA sequencing was conducted as previously described (Wyche, T. P.; Hou, Y.; Braun, D.; Cohen, H. C.; Xiong, M. P.; Bugni, T. S. *J. Org. Chem.* 2011, 76, 6542-6547). WMMB499 was identified as an *Actinomadura* sp. and demonstrated 99% sequence similarity to *Actinomadura* sp. 13679C (accession number EU741239).

The 16S sequence for WMMB499 was deposited in GenBank (accession number JX101467).

Fermentation, Extraction, and Isolation. Two 10 mL seed cultures (25×150 mm tubes) in medium ASW-A (20 g soluble starch, 10 g glucose, 5 g peptone, 5 g yeast extract, 5 g $CaCO_3$ per liter of artificial seawater) were inoculated with strain WMMB499 and shaken (200 RPM, 28° C.) for seven days. Two hundred fifty mL baffled flasks (3×50 mL) containing ASW-A were inoculated with 1 mL seed culture and were shaken (200 RPM, 28° C.) for seven days. Two-liter flasks (6×500 mL) containing medium ASW-A with Diaion HP20 (4% by weight) were inoculated with 25 mL from the 50 mL culture and shaken (200 RPM, 28° C.) for seven days. Filtered HP20 and cells were washed with $H_2O$ and extracted with acetone. The acetone extract (3.2 g) was subjected to liquid-liquid partitioning using 30% aqueous methanol (MeOH) and $CHCl_3$ (1:1). The $CHCl_3$-soluble partition (2.2 g) was fractionated by Sephadex LH20 column chromatography ($CHCl_3$:MeOH, 1:1). Fractions containing forazoline A (compound of Formula I, X=Cl) were subjected to RP HPLC (10/90% to 100/0% MeOH—$H_2O$ containing 0.1% acetic acid, 22 min) using a Phenomenex Gemini C18 column (100×30 mm, 5 μm), yielding forazoline A (20.1 mg, $t_R$ 12.5 min). For $^{13}C$ and $^{15}N$ incorporation, the same procedure was used (1×250 mL) with labeled medium ASW-A (20 g soluble starch, 10 g $U^{13}C$-glucose, 2.5 g peptone, 2.5 g yeast extract, 5 g $^{15}NH_4Cl$, 5 g $CaCO_3$ per liter of artificial seawater). For the incorporation of bromine and the production of forazoline B (compound of Formula I, X=Br), the same procedure was used with two-liter flasks (2×500 mL) containing medium ASW-A (with an increase of KBr from 0.1 g/L to 10 g/L and elimination of 20 g/L NaCl).

Acetylation. Forazoline A (1.0 mg) was dissolved in 150 μL pyridine, and 50 μL acetic anhydride was added to the solution. The solution was stirred at room temperature for 24 hours. The product was dried under argon.

Example 2

Biological Activity of Forazoline A

Animals. Six-week-old ICR Swiss specific-pathogen-free female mice weighing 23 to 27 g were used for all studies. Animals were maintained in accordance with the American Association for Accreditation of Laboratory Care criteria. Animal studies were approved by the University of Wisconsin Animal Care Committee.

Infection model. A neutropenic, murine, disseminated candidiasis model was used for the treatment studies. Mice were rendered neutropenic (polymorphonuclear cell counts of <100 $mm^3$) by injecting cyclophosphamide subcutaneously 4 days before infection (150 mg/kg of body weight) and 1 day before infection (100 mg/kg). Candida albicans K1 was subcultured on Sabouraud dextrose agar (SDA) 24 h prior to infection. The inocula were prepared by placing three to five colonies into 5 ml of sterile 0.15 M NaCl warmed to 35° C. The final inoculum was adjusted to 0.6 transmittance at 530 nm. Fungal counts of the inocula determined by viable counts on SDA were 5.63±0.38 $log_{10}$ CFU/mL (mean±standard deviation).

Disseminated infection with C. albicans organisms was produced by injection of 0.1 ml of the inoculum via the lateral tail vein 2 h prior to the start of antifungal therapy. At the end of the study period (8 h), animals were sacrificed by $CO_2$ asphyxiation. After sacrifice the kidneys of each mouse were immediately removed and placed in sterile 0.15 M NaCl at 4° C. The organs were homogenized and then serially diluted 1:10. Aliquots were plated onto SDA for viable fungal colony counts after incubation for 24 h at 35° C. The lower limit of detection was 100 CFU/kidney. The results are expressed as the mean and standard deviation of the $log_{10}$ CFU/kidney from three mice.

Drug Treatment. Groups of three mice were treated with either an intravenous or intraperitoneal single of forazoline A at 0.312, 1.25, and 5 mg/kg. The intravenous dose was given by the lateral tail vein via a 200 μL infusion. The intraperitoneal dose was administered in 500 μL volume. Control mice were treated with saline. Groups of mice were sacrificed at the start of therapy and 8 hours after therapy for determination of organism burden in the kidney as described above.

Results. Forazoline demonstrated in vivo efficacy in neutropenic (immunocompromised) mice in a disseminated candidiasis model against Candida albicans K1. Mice were treated with the compound at concentrations 2.5, 0.78, and 0.125 mg/kg. After 8 hours, the mice treated with the compound showed a decrease in greater than 1 $log_{10}$ cfu/kidney (1.5+/−0.12) reduction in organism burden compared to control mice. No toxic effects from the compound were apparent.

Example 3

Yeast Membrane Permeability

Forazoline A demonstrated a novel mechanism of action, as determined by chemical genomic profiling with the yeast Saccharomyces cerevisiae. This method has been used to explore the mechanism of action for bioactive compounds, including natural products. Forazoline A was screened against over four thousand deletion mutant yeast strains, genomic DNA was extracted, and mutant-specific DNA barcodes were amplified and sequenced by Illumina sequencing. Forazoline A sensitive and resistant mutants were determined by quantification of DNA-barcodes, which provided a chemical genomic profile used to evaluate the mechanism of action.

The top sensitive mutant strains (P<0.0001) were significantly enriched for genes involved in phospholipid translocation (GO: 0045332, P=0.0009). This enrichment was driven by sensitive mutants with deletions of the genes LEM3 and FPK1. Enzymes Lem3p formed complexes with Dnf1p/Dnf2p, which is responsible for maintaining phospholipid asymmetry in membranes while Fpk1p is a Ser/Thr protein kinase that regulates Lem3p-Dnf1p/Dnf2p (Dnf1p is a phospholipid translocase). The data suggests that forazoline A either directly affects phospholipids or interacts with a protein target that complements the activity of the Lem3p complexes. An important aspect of the data was that the mutant LEM3-Δ was not among the most sensitive strains for caspofungin, fluconazole, or amphotericin, which suggests that forazoline A has a unique mechanism of action from known antifungal agents.

Figure 12:
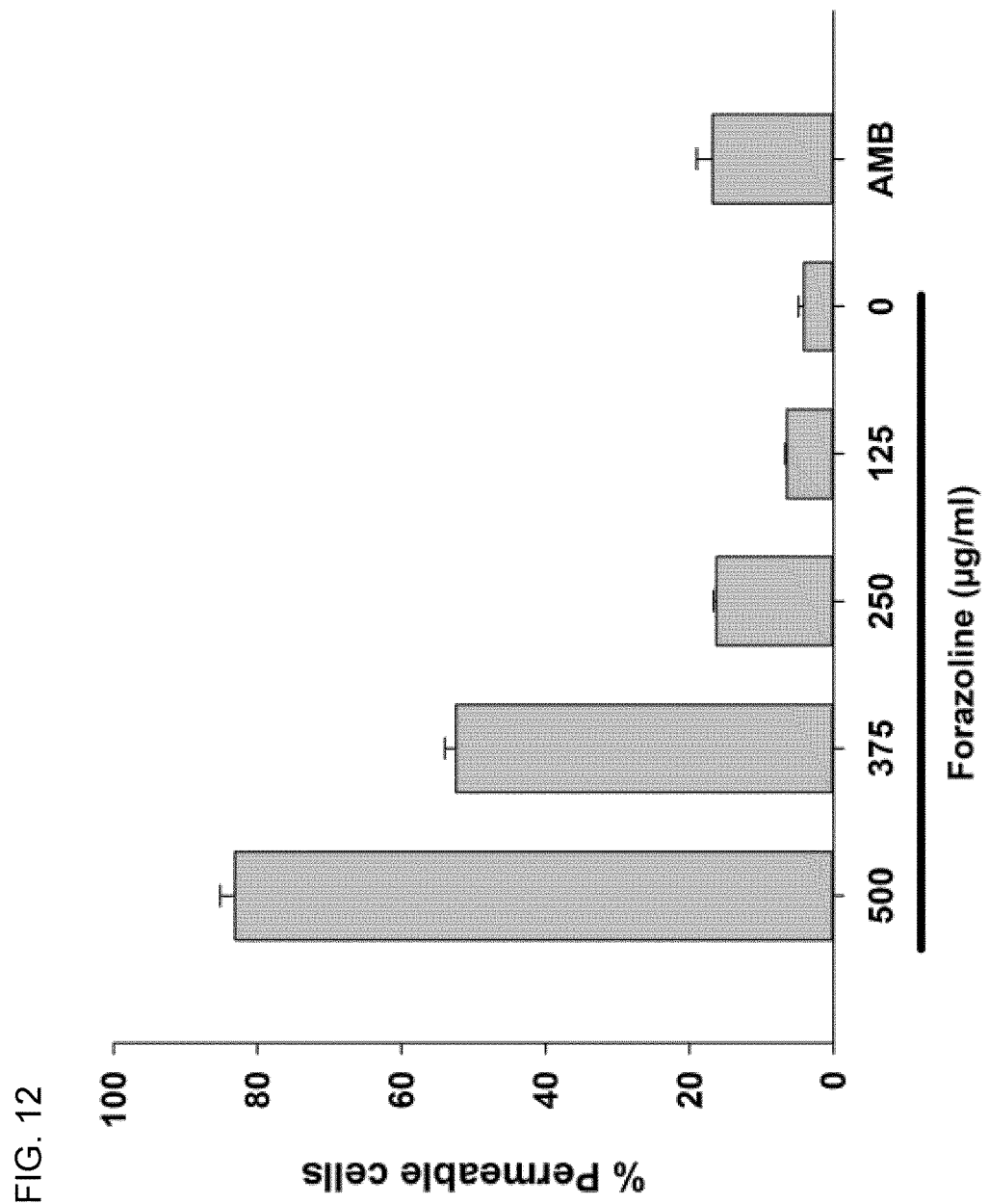
FIG. 12 shows the fungal membrane permeability of Forazoline A and shows a comparison of the potency of Forazoline A to amphotericin B (AMB).

The membrane integrity of yeast cells treated with forazoline A was investigated through the evaluation of membrane permeability. As shown in FIG. 12, the results demonstrated that forazoline A caused a dose dependent permeabilization of fungal membranes after 4 h of treatment, but at the same concentration as amphotericin B (AMB) (125 μg/mL) was less potent.

Since chemical genomics suggested that forazoline A had a different mechanism compared to AMB, synergy studies were conducted. Forazoline A showed synergy when tested with AMB indicating a parallel and/or complementary mechanism of action. The data indicated that membrane integrity was affected by forazoline A.

Example 4

Structure Elucidation

Analytical data were gathered for forazoline A, including optical rotation, IR, HRMS and NMR spectra.

Figure 2:
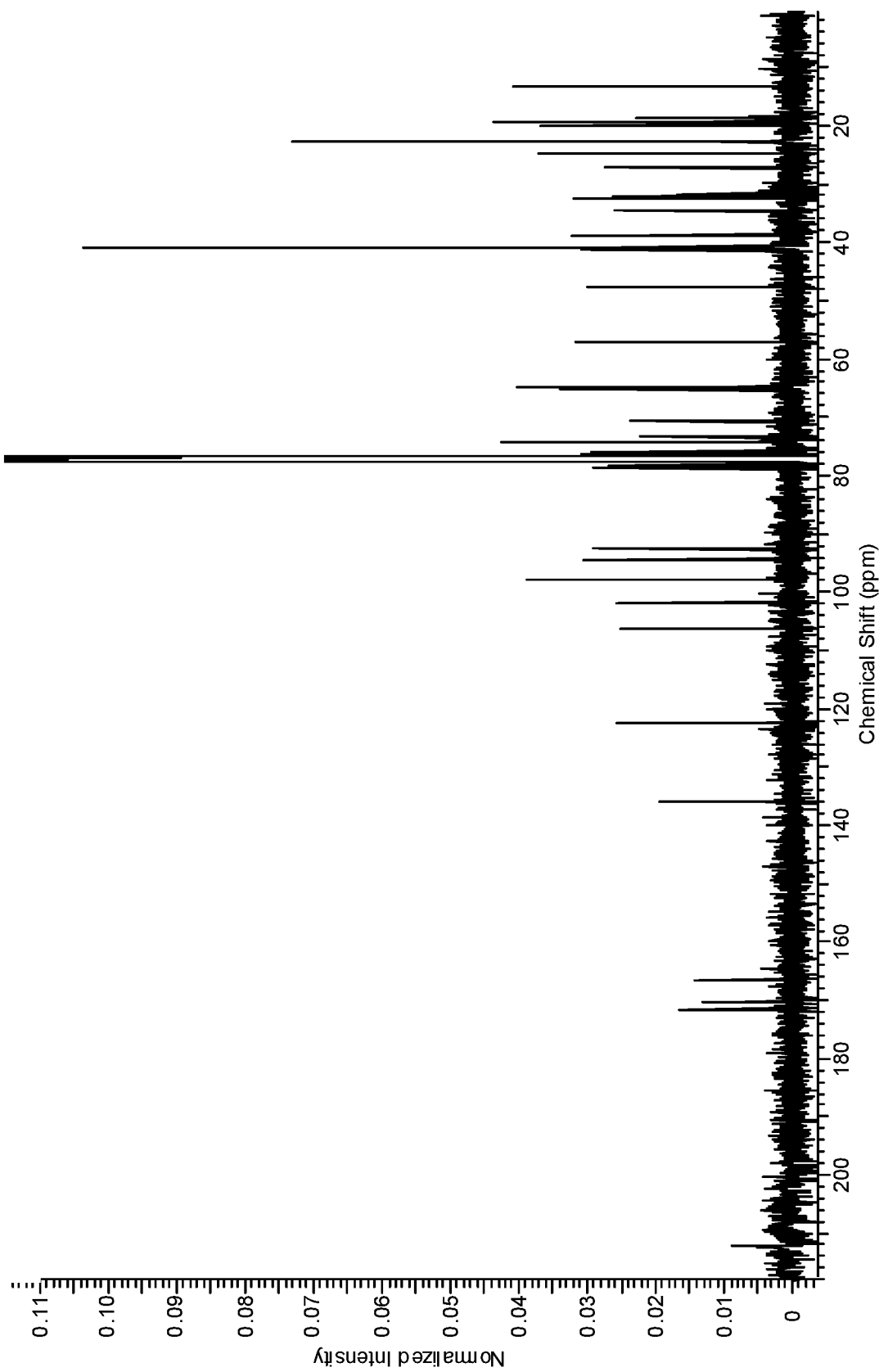
FIG. 2 shows a $^{13}C$ NMR (125 MHz, CDCl$_3$) spectrum of Forazoline A.
Figure 7:
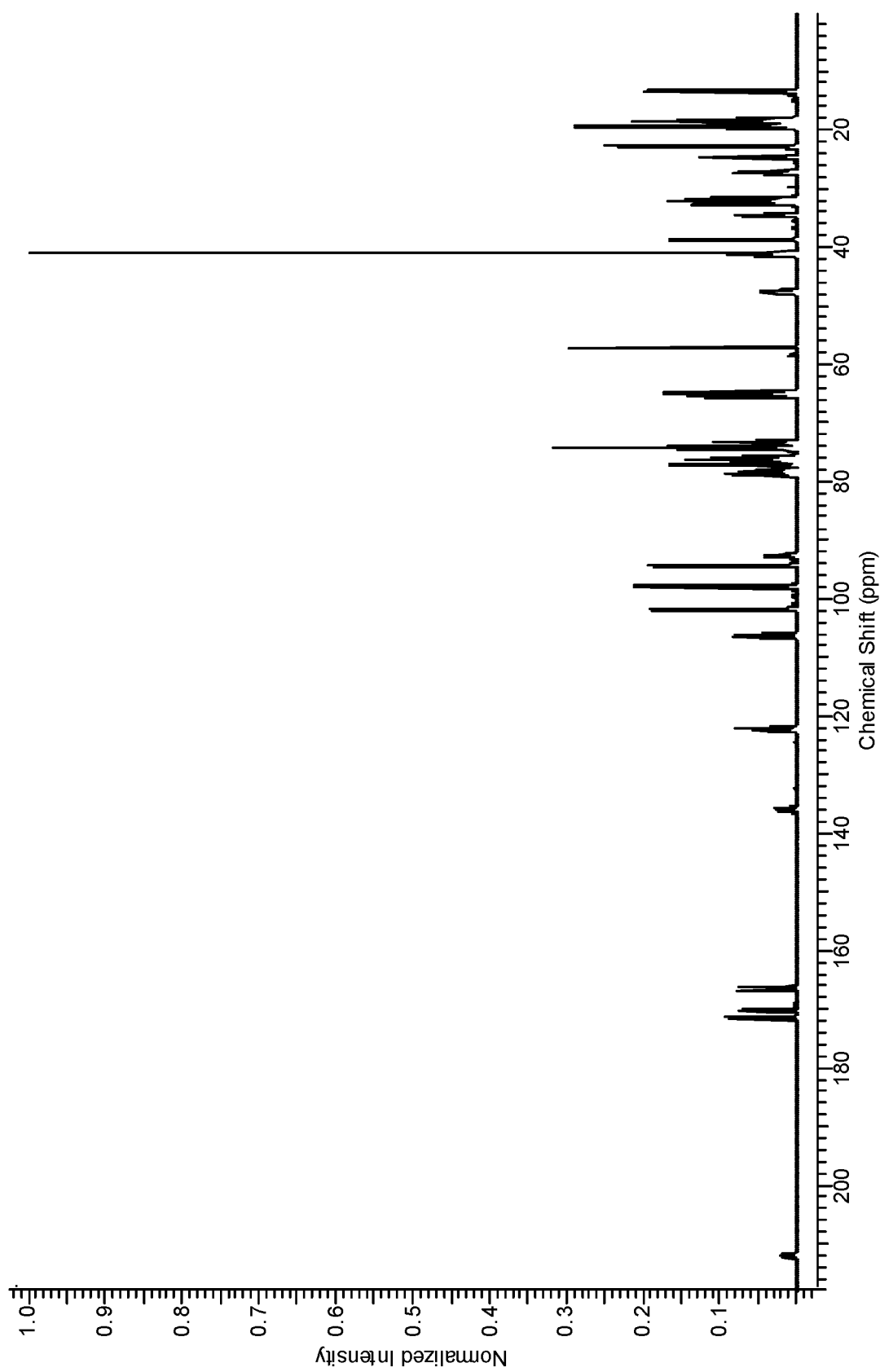
FIG. 7 shows a $^{13}C$ NMR (125 MHz, CDCl$_3$) spectrum of ($^{13}C$-labeled) Forazoline A.
Figure 10:
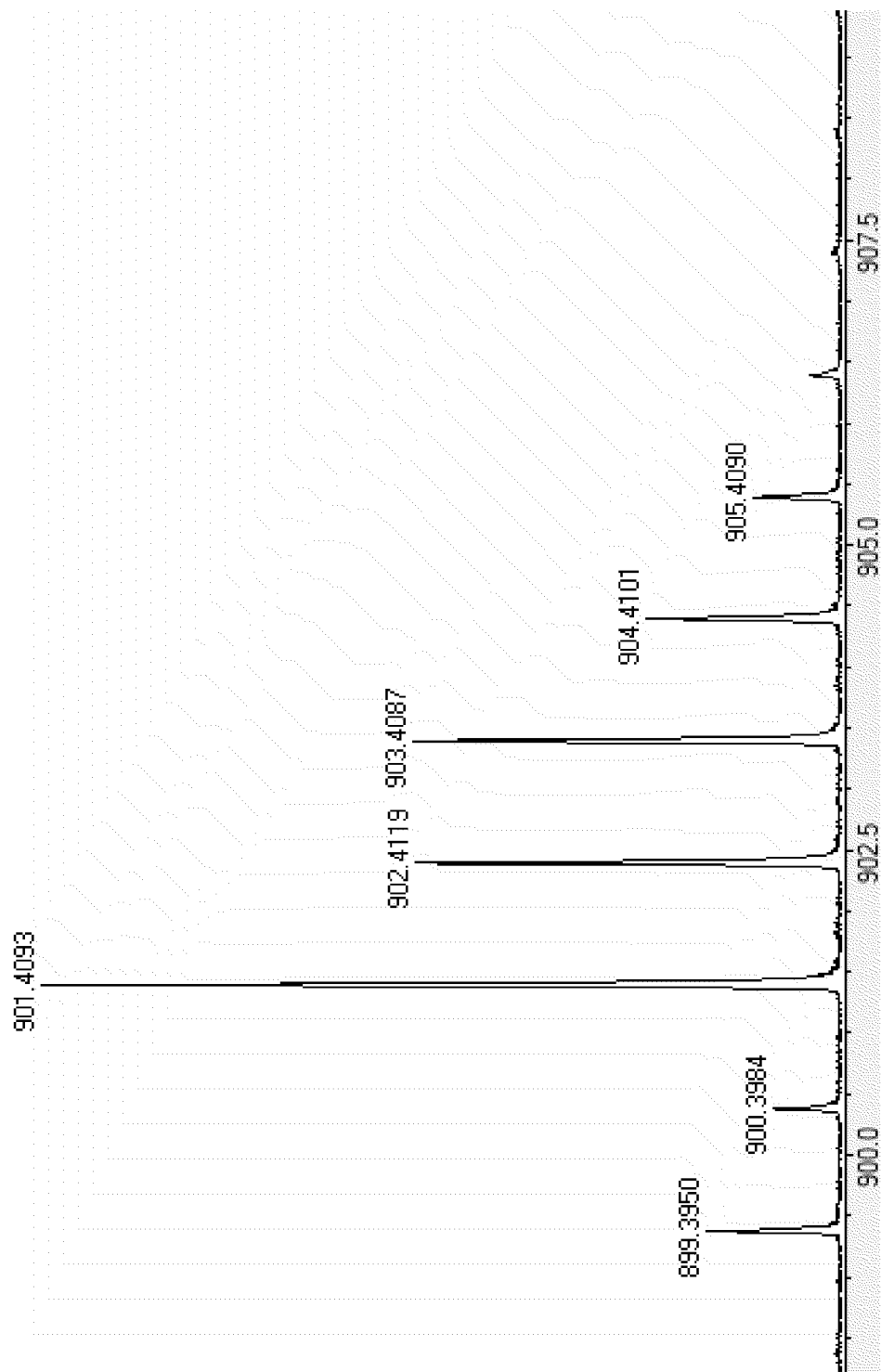
FIG. 10 shows a HRMS spectrum of Forazoline A.
Figure 11:
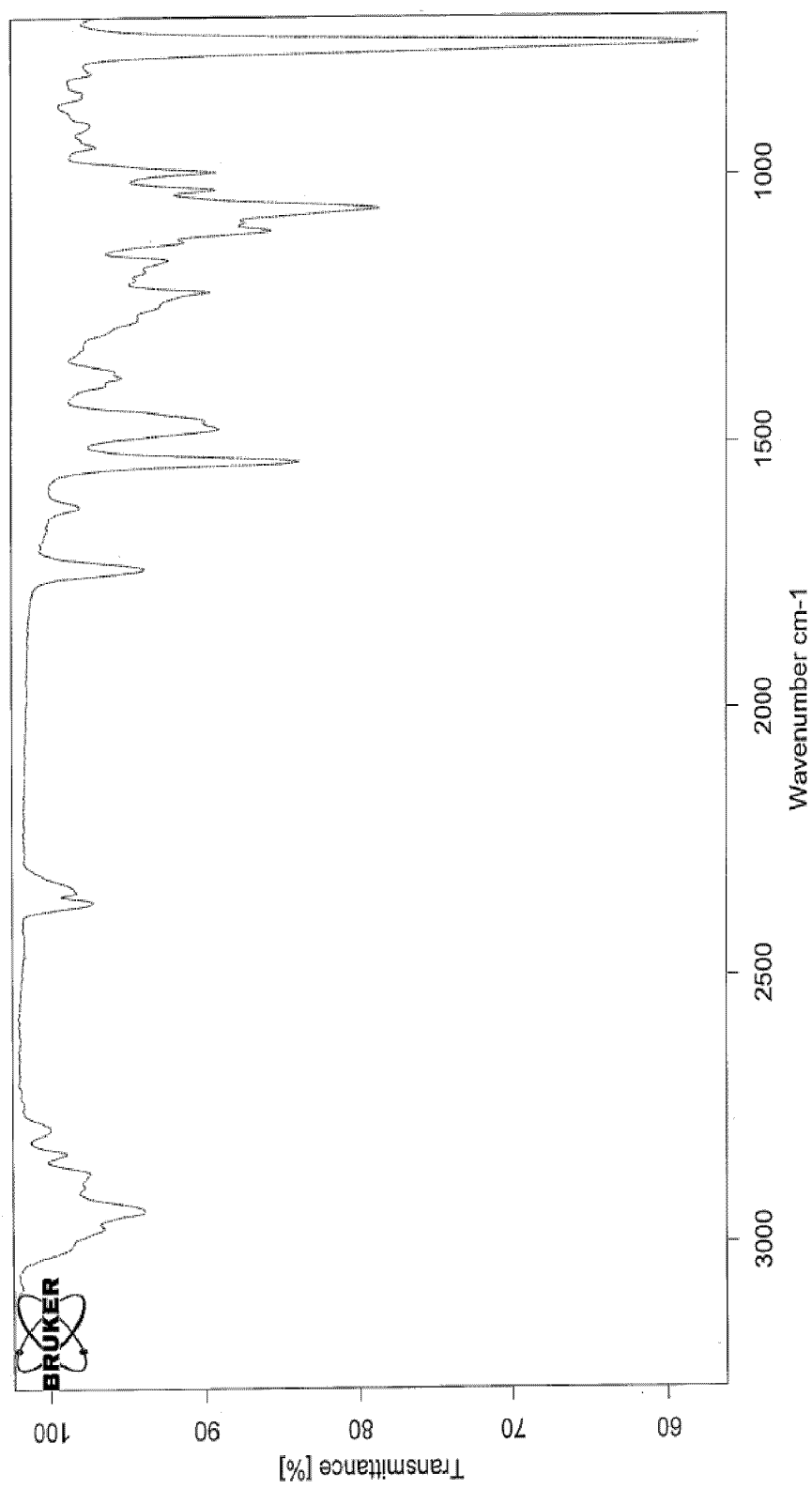
FIG. 11 shows an IR spectrum of Forazoline A.

Forazoline A (compound of Formula I, X=Cl): yellow solid; $[\alpha]^{25}_D$+300 (c 0.6, MeOH); UV (MeOH) $\lambda_{max}$ (log ε) 205 (4.11), 222 (3.91), 254 (3.74), 274 (3.54), 406 (4.05) nm; IR (ATR) (see FIG. 11) $U_{max}$ 2940, 2359, 1733, 1533, 1472, 1060 cm$^{-1}$; $^1$H and $^{13}$C NMR (See Table 1 and FIGS. 1, 2 and 7); HRMS [M+H]$^+$ m/z 901.4093 (calc'd for $C_{43}H_{70}ClN_4O_{10}S_2$, 901.4216) (see FIG. 10).

TABLE 1

$^1$H and $^{13}$C NMR data (600 MHz, CDCl$_3$)

Forazoline A

| Position | $\delta_c$, mult. | $\delta_H$ (J in Hz) | COSY* | HMBC** |
|---|---|---|---|---|
| 1 | 40.9, CH$_3$ | 2.22, s | | 2, 3 |
| 2 | 40.9, CH$_3$ | 2.22, s | | 1, 3 |
| 3 | 65.0, CH | 2.26, m | 4, 6 | 5 |
| 4 | 74.2, CH | 3.47, m | 3, 5 | 5, 8 |
| 5 | 19.4, CH$_3$ | 1.28, d (6.3) | 4 | 3, 4 |
| 6 | 18.7, CH$_2$ | 1.48, m | 3, 7 | 3, 7, 8 |
| | | 1.85, m | | |
| 7 | 32.6, CH$_2$ | 1.65, m | 6, 8 | |
| | | 1.95, m | | |
| 8 | 97.9, CH | 4.76, dd (1.9, 9.4) | 7 | 7, 9 |
| 9 | 92.6, C | | | |
| 10 | 22.8, CH$_3$ | 1.75, s | | 9, 10, 44 |
| 11 | 78.8, CH | 4.19, d (10.1) | 11 | 12 |
| 12 | 27.3, CH$_2$ | 1.30, m | 10, 12 | 10, 14 |
| | | 1.69, m | | |
| 13 | 32.1, CH$_2$ | 2.05, m | 11, 16 | 11, 14, 16 |
| | | 2.16, m | | |
| 14 | 136.0, C | | | |
| 15 | 19.9, CH$_3$ | 1.63, s | 16 | 12, 14, 16 |
| 16 | 122.4, CH | 5.08, d (9.4) | 12, 15, 17 | 13, 15 |
| 17 | 47.8, CH | 2.33, q (9.8) | 16, 18 | 14, 16, 18, 31, 32 |
| 18 | 73.4, CH | 4.04, m | 17, 27 | 16, 19, 27 |
| 19 | 101.8, CH | 4.91, dd (1.3, 9.1) | 20 | 18, 20 |
| 20 | 31.7, CH$_2$ | 1.30, m | 19, 21 | 19, 21 |
| 21 | 18.7, CH$_2$ | 1.58, m | 20, 22 | |
| | | 1.81, m | | |
| 22 | 65.4, CH | 2.15, m | 21, 25 | |
| 23 | 40.9, CH$_3$ | 2.22, s | | 22, 24 |
| 24 | 40.9, CH$_3$ | 2.22, s | | 22, 23 |
| 25 | 74.3, CH | 3.48, m | 22, 26 | 19, 26 |
| 26 | 19.3, CH$_3$ | 1.26, d (8.8) | 25 | 22, 25 |
| 27 | 34.7, CH$_2$ | 1.90, m | 18, 28 | 17, 29 |
| | | 2.08, m | | |
| 28 | 78.2, CH | 5.33, t (2.7) | 27 | 18, 29, 30, 31, 33 |
| 29 | 75.9, C | | | |
| 30 | 22.8, CH$_3$ | 1.53, s | | 29, 31 |
| 31 | 41.4, CH | 1.90, m | 32 | 16, 17, 29, 30, 32 |
| 32 | 13.4, CH$_3$ | 0.76, d (6.9) | 31 | 17, 29, 31 |
| 33 | 171.6, C | | | |
| 34 | 76.3, CH | 5.50, dd (4.1, 10.4) | 35 | 33, 35, 36, 38, 40 |

TABLE 1-continued $^1$H and $^{13}$C NMR data (600 MHz, CDCl$_3$)

Forazoline A

| Position | $\delta_c$, mult. | $\delta_H$ (J in Hz) | COSY* | HMBC** |
|---|---|---|---|---|
| 35 | 38.8, CH$_2$ | 3.80, t (11.2) | 34 | 33, 34 |
| | | 3.94, dd (4.1, 11.3) | | |
| 36 | 170.3, C | | | |
| 38 | 76.2, C | | | |
| 39 | 24.8, CH$_3$ | 1.59, s | | 36, 37, 39 |
| 40 | 94.4, CH | 5.04, s | NH | 37, 38, 41, 43 |
| 41 | 57.2, CH$_3$ | 3.40, s | | 39 |
| 42 | 166.5, C | | | |
| 43-NH | | 14.58, s | 39 | 37, 39, 41, 43 |
| 44 | 106.4, CH | 7.30, s | | 39, 41 |
| 45 | 212.0, C | | | |

Figure 3:
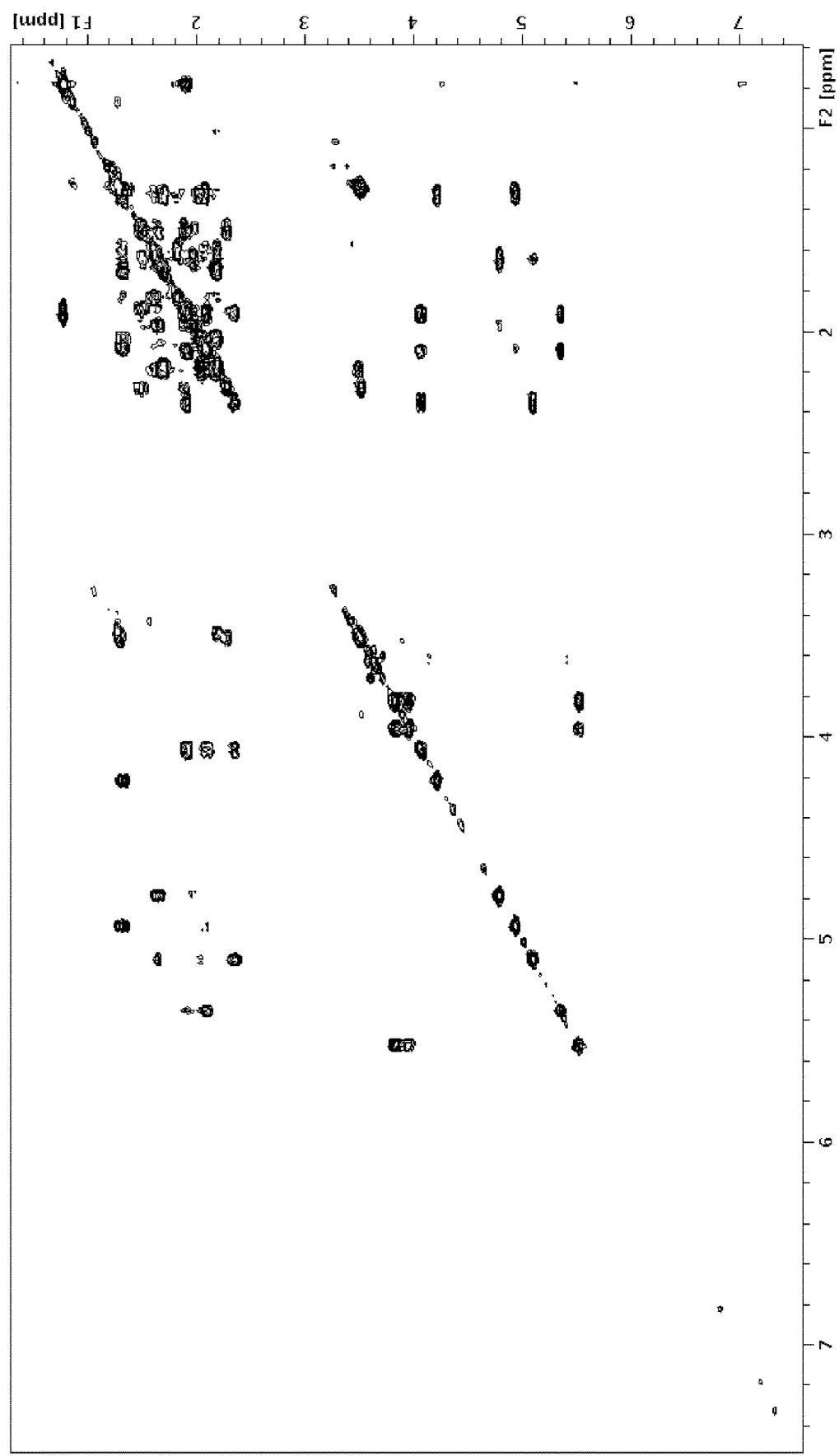
FIG. 3 shows a gCOSY (600 MHz, CDCl$_3$) spectrum of Forazoline A.
Figure 5:
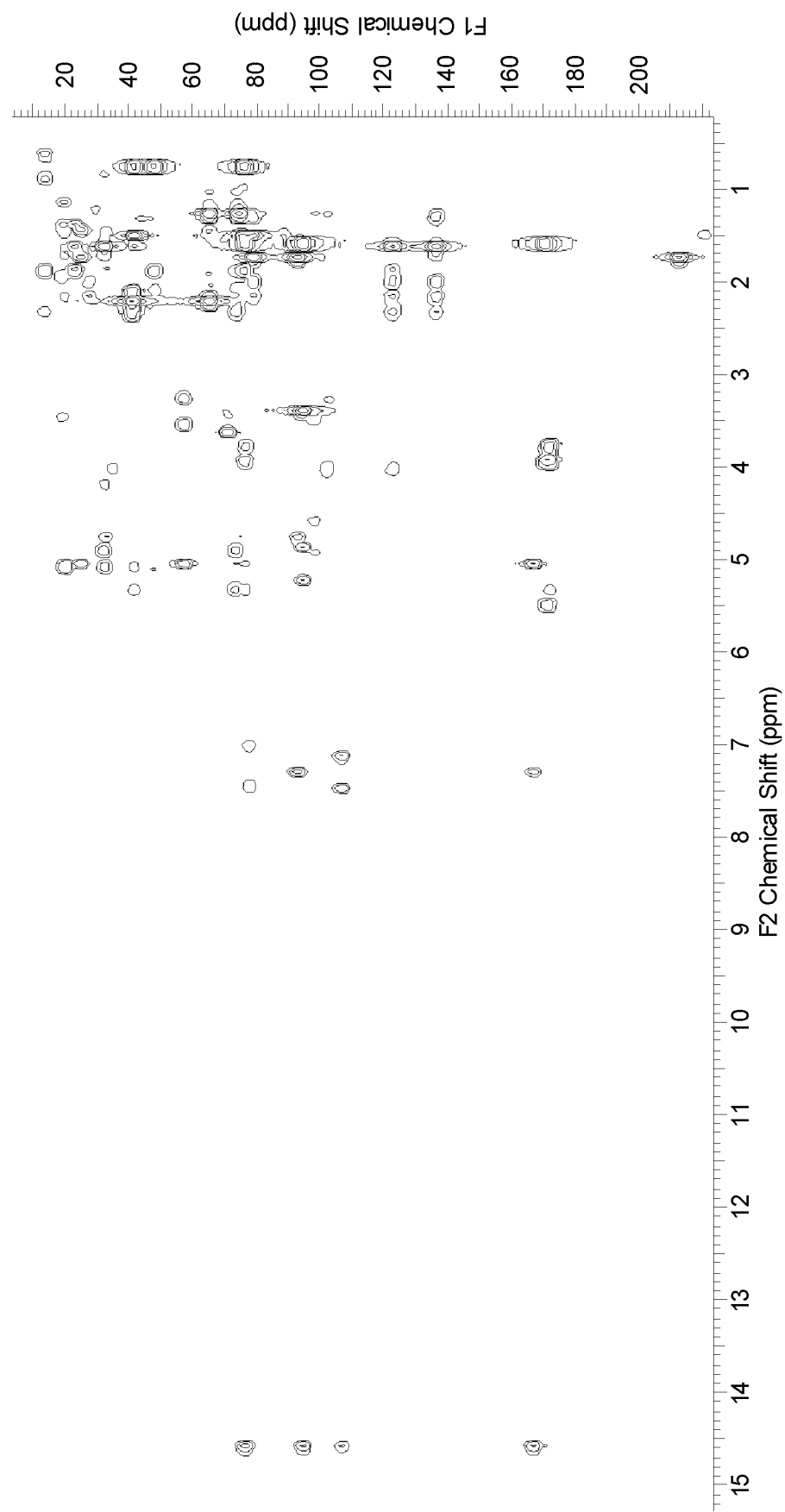
FIG. 5 shows a gHMBC (600 MHz, CDCl$_3$) spectrum of Forazoline A.
Figure 6:
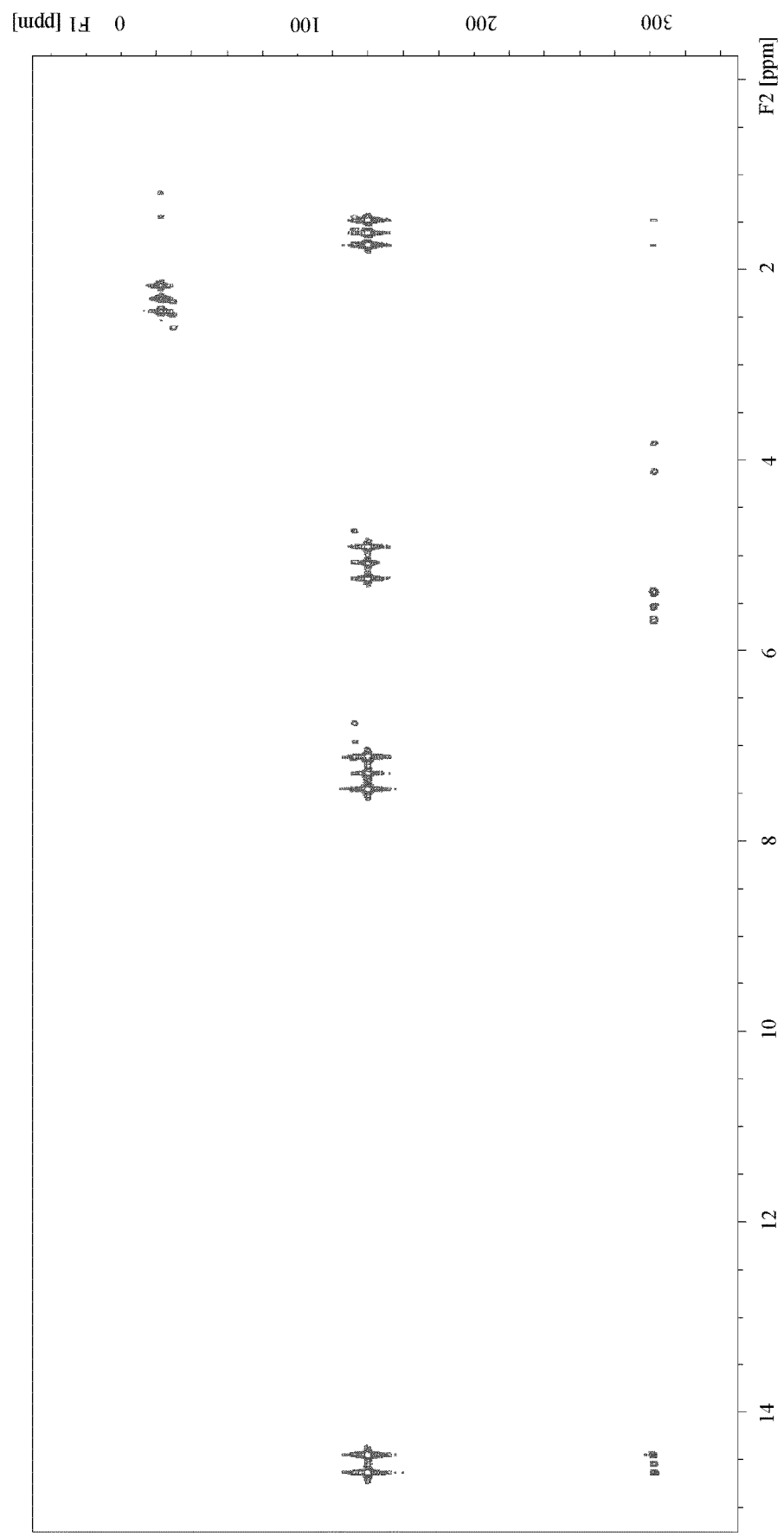
FIG. 6 shows a $^1H$-$^{15}N$ HMBC (500 MHz, CDCl$_3$) spectrum of ($^{15}N$-labeled) Forazoline A.

*See FIG. 3.
**See also FIGS. 5 and 6.

Figure 8:
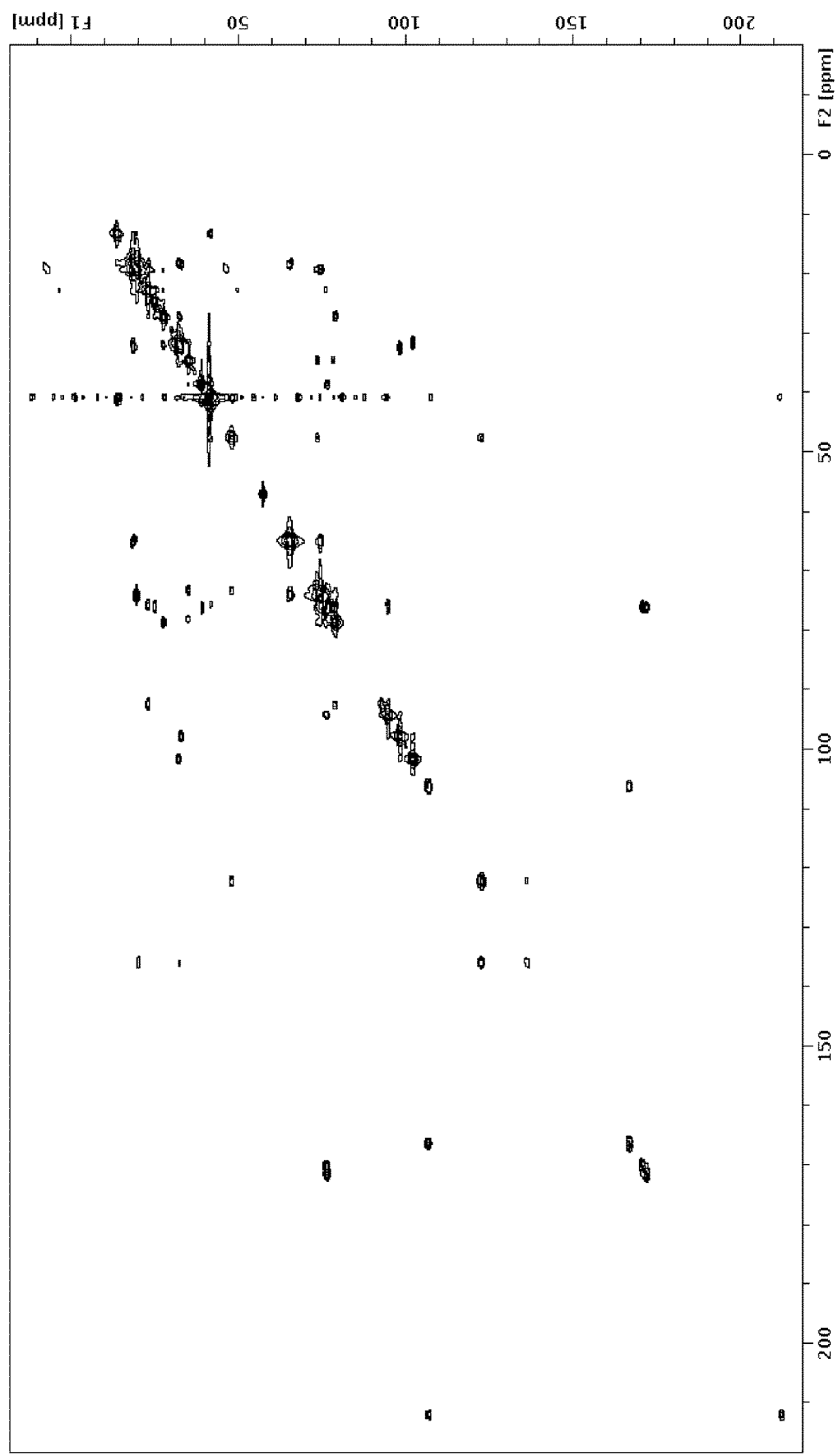
FIG. 8 shows a $^{13}C$-$^{13}C$ COSY (125 MHz, CDCl$_3$) spectrum of ($^{13}C$-labeled) Forazoline A.

Discussion: HRMS supported the molecular formula of $C_{43}H_{69}ClN_4O_{10}S_2$ for forazoline A (compound of Formula I). Extensive 1D and 2D NMR data (Table 1) were analyzed to establish the majority of the planar structure, but the presence of several quaternary centers prevented complete elucidation of the structure. The carbon backbone of the structure was determined by increasing the $^{13}$C abundance with uniformly-labeled $^{13}$C glucose and acquiring a $^{13}$C-$^{13}$C gCOSY. Fermentation of WMMB499 in ASW-A with $^{13}$C-labeled glucose and subsequent purification (see above), yielded forazoline A with nearly 75% $^{13}$C incorporation. The $^{13}$C-$^{13}$C gCOSY was acquired in 30 minutes on 7.0 mg forazoline A and allowed for complete assignment of the carbon backbone (see FIG. 8).

Figure 9:
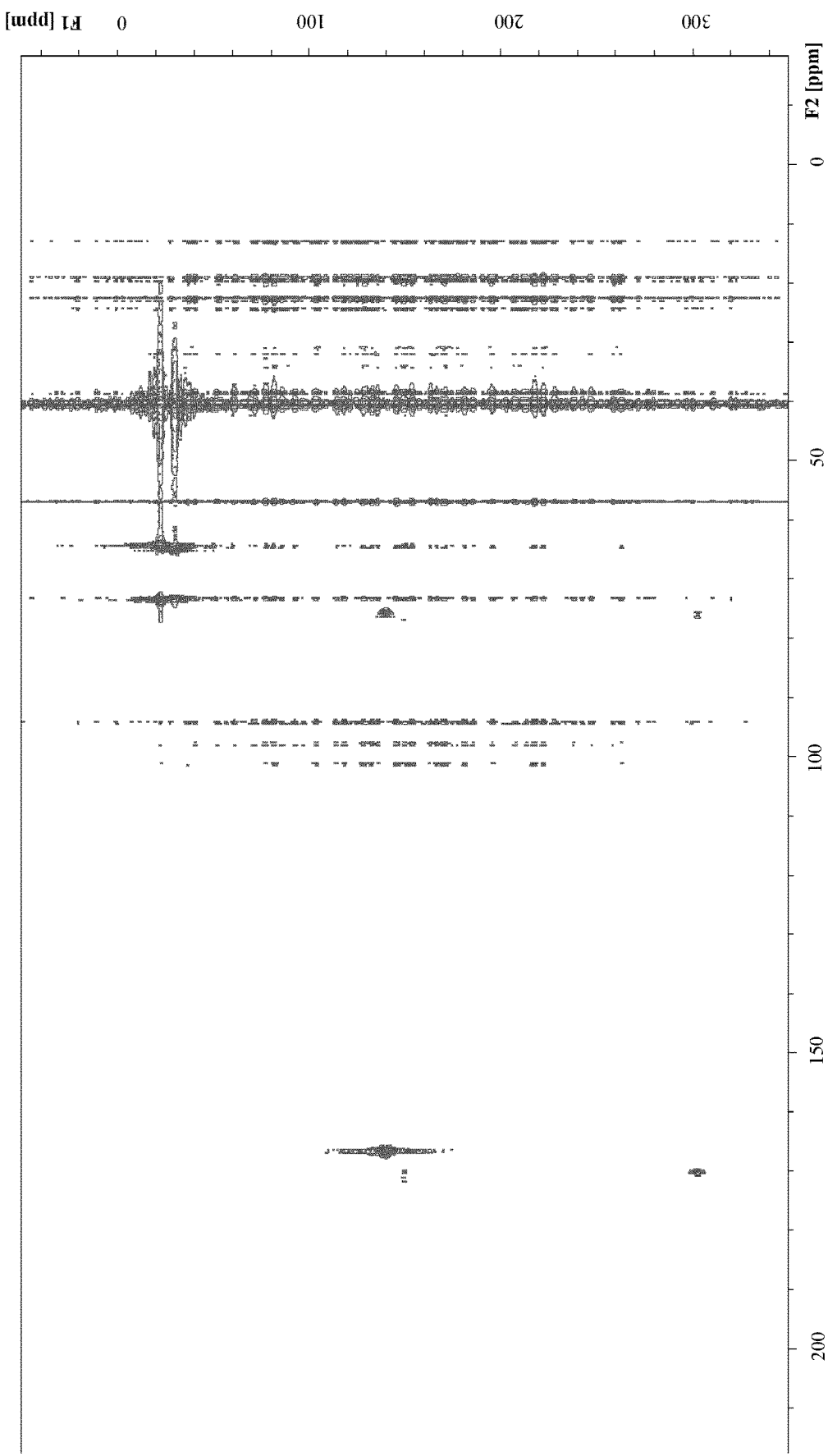
FIG. 9 shows a $^{13}C$-$^{15}N$ NMR spectrum of ($^{13}C$-, $^{15}N$-labeled) Forazoline A.

Despite knowing the carbon backbone, the entire structure could not be elucidated due to a portion of the structure composed of several rings that contained multiple heteroatoms—oxygen, nitrogen, and sulfur. The $^{13}$C chemical shifts of several carbon atoms attached to heteroatoms did not conclusively indicate which heteroatoms were attached to each carbon. Therefore, a method was pursued to determine the $^{13}$C-$^{15}$N connectivity. Fermentation of 250 mL of WMMB499 in a variation of ASW-A, containing $^{15}$NH$_4$Cl and uniformly-labeled $^{13}$C-glucose (see above), allowed for the production of $^{13}$C- and $^{15}$N-labeled forazoline A. A 2D NMR experiment was then developed to determine the $^{13}$C-$^{15}$N connectivity (see FIG. 9). The spectrum revealed that N-43 ($\delta_N$ 140.2 ppm) was attached to C-42 ($\delta_C$ 166.5) and C-38 ($\delta_C$ 76.2 ppm), and N-37 ($\delta_N$ 302.6 ppm) was attached to C-36 ($\delta_C$ 170.3 ppm) and C-34 ($\delta_C$ 78.2 ppm); the spectrum also confirmed the presence of two N-dimethyl groups. The downfield shift of N-37, combined with the knowledge that it was connected to only two carbons, suggested the presence of an imine.

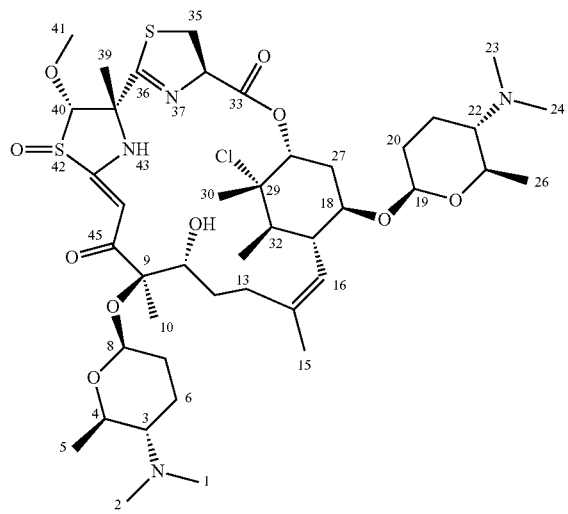 [SMILES: CO[C@H]1S(=O)/C2=C\C(=O)[C@](C)(O[C@H]3CC[C@H](N(C)C)[C@@H](C)O3)[C@H](O)CC/C(C)=C\[C@@H]3[C@@H](C)[C@](C)(Cl)[C@@H](C[C@H]3O[C@H]3CC[C@H](N(C)C)[C@@H](C)O3)OC(=O)[C@@H]3CSC(=N3)[C@]1(C)N2]

Figure 4:
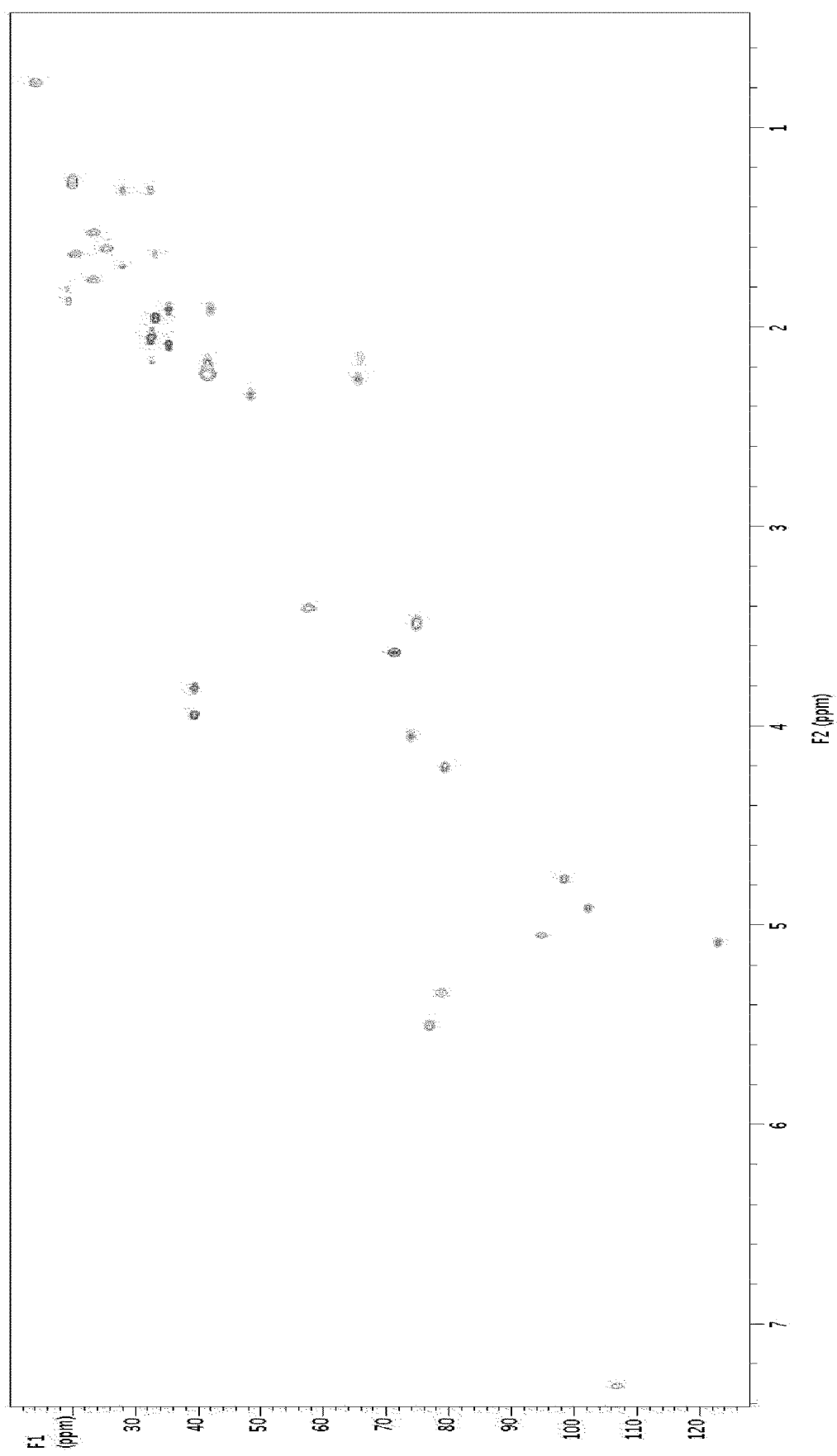
FIG. 4 shows a gHSQC (600 MHz, CDCl$_3$) spectrum of Forazoline A.

HRMS of forazoline A in CD$_3$OD and D$_2$O revealed the presence of two exchangeable protons. Acquisition of a $^1$H-$^{15}$N HSQC (FIG. 4) allowed us to conclude that one of the exchangeable protons was an amine ($\delta_H$ 14.58, $\delta_N$ 170.3). To determine the location of the other exchangeable proton, forazoline A was acetylated. Two major products, with one and two acetyl units, were formed, and acquisition of 1D and 2D NMR, determined that the other exchangeable proton was attached to a heteroatom at C-11. The chemical shift ($\delta_C$ 78.8) at C-11 determined that exchangeable was a hydroxyl.

The HRMS isotopic distribution and molecular formula suggested the presence of one chlorine atom. To determine the location of the chlorine atom, the amount of KBr in fermentation medium ASW-A was increased from 0.1 g/L to 10 g/L to produce a brominated analog, forazoline B (compound of Formula I, X=Br). HRMS of forazoline B supported the molecular formula of C$_{43}$H$_{69}$BrO$_{10}$N$_4$S$_2$. A comparison of the $^1$H and $^{13}$C NMR shifts of forazolines A and B showed that the chemical shifts of H-28, H-31, C-28, and C-31 shifted downfield, and C-29 shifted upfield in forazoline B. No other significant changes in chemical shifts between forazoline A and B existed. Combining this knowledge with the fact that C-29 was a methine attached to two carbons, allowed us to conclude that the halogen atom was located at C-29.

The presence of the sulfoxide was determined by a combination of IR and DFT calculations. Sulfoxides typically demonstrate an IR band between 1015-1060 cm$^{-1}$. A band at 1060 cm$^{-1}$ in the IR spectrum of forazoline A suggested the presence of a sulfoxide. Additionally, the aforementioned NMR data, which provided $^{13}$C-$^{13}$C and $^{13}$C-$^{15}$N connectivity, limited the number of locations for this oxygen. In order to determine which sulfur atom in the molecule contained the sulfoxide, molecular modeling and DFT calculations were used to calculate theoretical NMR shifts, which could then be compared to the experimental data. Molecular modeling and DFT calculations were performed as previously described (Wyche, T. P.; Hou, Y.; Braun, D.; Cohen, H. C.; Xiong, M. P.; Bugni, T. S. J. Org. Chem. 2011, 76, 6542-6547 (incorporated by reference herein)). The DP4 probability method allowed for comparison of the theoretical NMR shifts of the two potential structures with the experimental data. Using all $^{13}$C NMR shifts, the DP4 probability calculated that the theoretical NMR data for the sulfoxide attached to C-39 and C-41 matched the experimental NMR data better than the theoretical NMR data for the sulfoxide attached to C-35 and C-36 (See Table 1 and FIGS. 2, and 7-9 ($^{13}$C NMR shifts)).

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:
1. A pharmaceutical composition comprising an effective amount of a compound of Formula I:

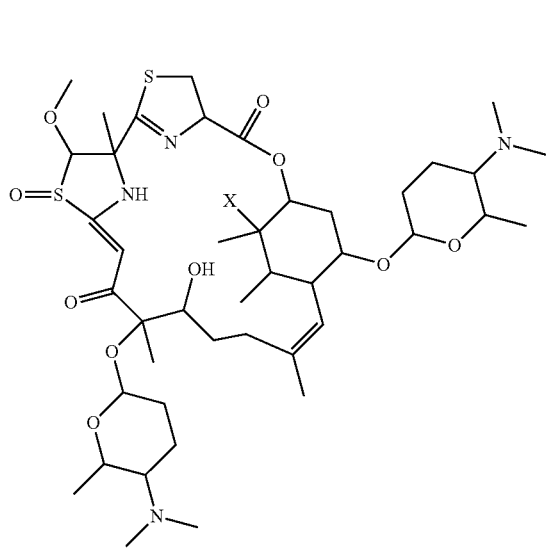

or pharmaceutically acceptable salt thereof for treating a fungal infection in a mammal, wherein X is Cl or Br; and
a pharmaceutically acceptable carrier.

2. The pharmaceutical composition of claim 1, formulated for oral, parenteral, nasal, or topical administration.

3. The pharmaceutical composition of claim 1, wherein the mammal is human.

4. The pharmaceutical composition of claim 1, further comprising amphotericin B, ketoconazole, terbinafine, nystatin, fluconazole, itraconazole, or nystatin.

5. The pharmaceutical composition of claim 1, wherein the compound of Formula I has the Formula IA:

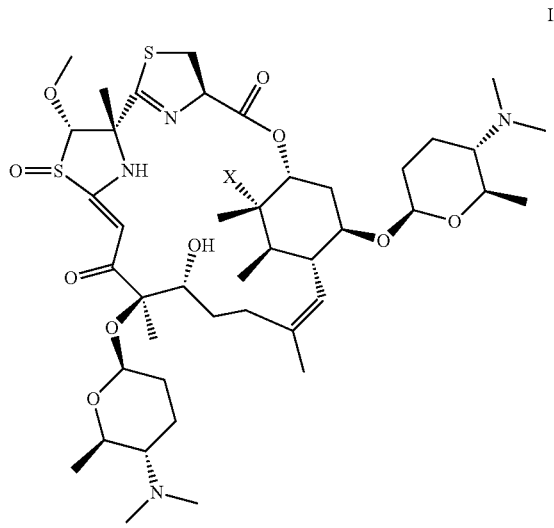

wherein X is Cl or Br.

6. The pharmaceutical composition of claim 5, wherein the mammal is human.

7. The pharmaceutical composition of claim 1, wherein the compound of Formula I has the Formula IB:

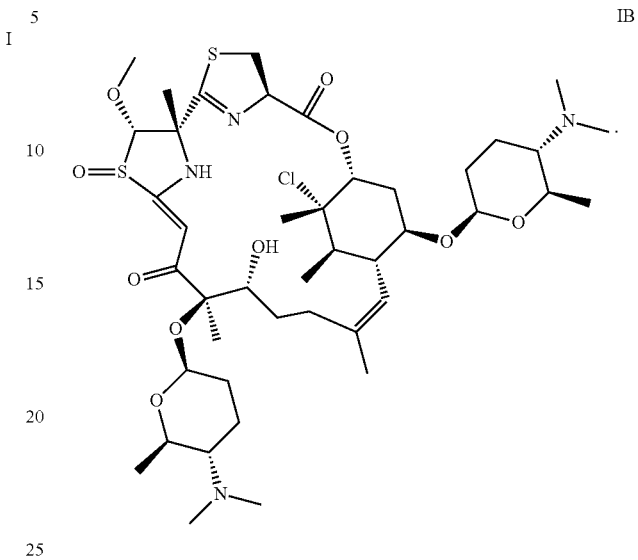

8. The pharmaceutical composition of claim 7, wherein the mammal is human.

9. The pharmaceutical composition of claim 1, wherein the pharmaceutical composition comprises an effective amount of the compound or pharmaceutically acceptable salt thereof for treating a *Candida* infection.

10. The pharmaceutical composition of claim 9, wherein the mammal is human.

11. The pharmaceutical composition of claim 1, wherein the pharmaceutical composition comprises an effective amount of the compound or pharmaceutically acceptable salt thereof for treating a *Candida albicans* infection in a human.

12. A pharmaceutical composition comprising an effective amount of a compound of Formula I:

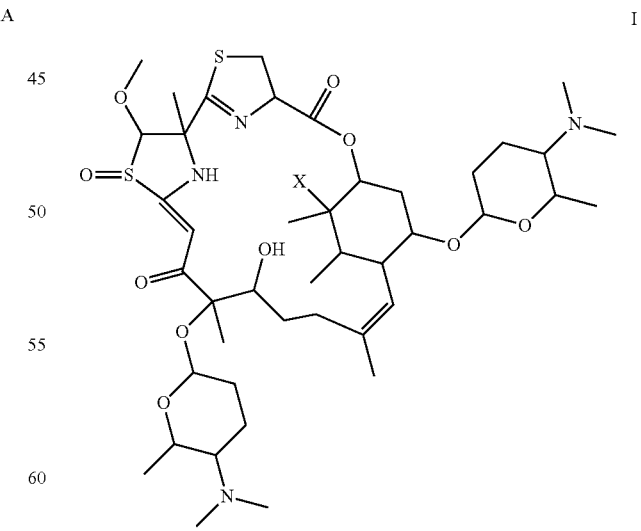

or pharmaceutically acceptable salt thereof for treating a fungal infection in a mammal, wherein X is Cl or Br; and
an isotonic aqueous solution.

13. The pharmaceutical composition of claim 12, formulated for parenteral administration.

14. The pharmaceutical composition of claim 12, wherein the mammal is human.

15. The pharmaceutical composition of claim 12, wherein the compound of Formula I has the Formula IA:

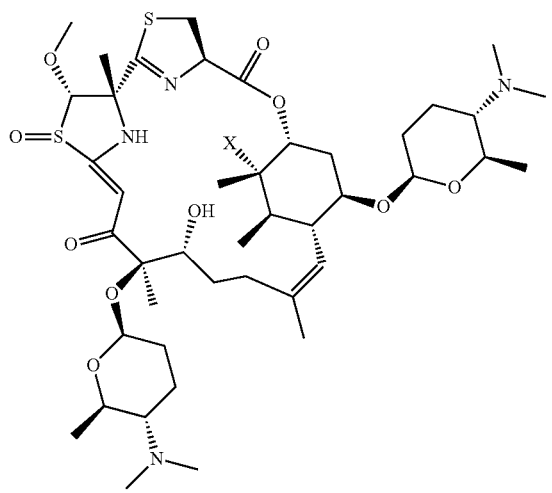

IA wherein X is Cl or Br.

16. The pharmaceutical composition of claim 12, wherein the compound of Formula I has the Formula IB:

IB

17. The pharmaceutical composition of claim 12, wherein the pharmaceutical composition comprises an effective amount of the compound or pharmaceutically acceptable salt thereof for treating a *Candida* infection.

18. The pharmaceutical composition of claim 12, wherein the pharmaceutical composition comprises an effective amount of the compound or pharmaceutically acceptable salt thereof for treating a *Candida albicans* infection.

19. A pharmaceutical composition comprising an effective amount of a compound of Formula I:

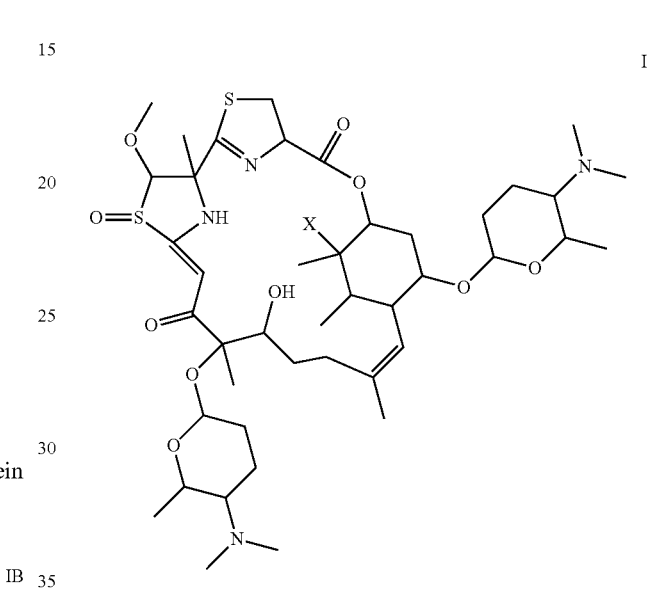

I or pharmaceutically acceptable salt thereof for treating a fungal infection in a mammal, wherein X is Cl or Br; and one or more of cetyl esters wax, cetyl alcohol, white wax, glyceryl monostearate, propylene glycol monostearate, methyl stearate, benzyl alcohol, sodium lauryl sulfate, glycerin, mineral oil, carbomer, ethyl alcohol, acrylate adhesives, polyisobutylene adhesives, and silicone adhesives.

20. The pharmaceutical composition of claim 19, wherein the mammal is human.

21. The pharmaceutical composition of claim 19, further comprising amphotericin B, ketoconazole, terbinafine, nystatin, fluconazole, itraconazole, or nystatin.

* * * * *